United States Patent [19]

Davis, Jr.

[11] 4,370,493

[45] Jan. 25, 1983

[54] SYNTHESIS OF ALPHA-AMINO ACIDS

[75] Inventor: Jefferson W. Davis, Jr., San Francisco, Calif.

[73] Assignee: The United States of America as represented by the Secretary of Energy, Washington, D.C.

[21] Appl. No.: 278,106

[22] Filed: Jun. 29, 1981

Related U.S. Application Data

[62] Division of Ser. No. 77,811, Sep. 21, 1979, abandoned.

[51] Int. Cl.$^3$ ............................................. C07C 99/10
[52] U.S. Cl. ................................... 562/444; 562/443; 562/445; 562/575; 260/465.6; 260/465 F; 260/465 E; 260/465.5 R; 260/456 NS
[58] Field of Search ................... 260/465 G, 465–467, 260/465.5 R, 465.6, 456 NS; 562/443–449, 507, 575

[56] References Cited

U.S. PATENT DOCUMENTS

| | | | |
|---|---|---|---|
| 2,264,026 | 11/1941 | Gudgeon et al. | 260/464 |
| 2,331,681 | 10/1943 | Hechenbleikner | 260/465.7 |
| 2,446,651 | 8/1948 | Hartung | 562/444 |
| 2,520,312 | 8/1950 | Gresham et al. | 562/442 |
| 2,917,541 | 12/1959 | Anatol et al. | 562/444 |
| 3,133,115 | 5/1964 | Proskon | 260/465.7 |
| 3,179,684 | 4/1965 | Covey et al. | 260/456 |
| 3,215,736 | 11/1965 | Guinot | 562/575 |
| 3,272,854 | 9/1966 | Covey et al. | 260/456 |
| 3,311,534 | 3/1967 | Covey et al. | 424/304 |
| 3,475,489 | 10/1969 | duGroaf et al. | 562/575 |
| 3,481,970 | 12/1969 | Griffith et al. | 260/465.7 |
| 4,243,814 | 1/1980 | Pascal et al. | 562/575 |

FOREIGN PATENT DOCUMENTS

| | | | |
|---|---|---|---|
| 2343599 | 3/1975 | Fed. Rep. of Germany | 562/575 |
| 7310844 | 2/1974 | Netherlands | 562/575 |

OTHER PUBLICATIONS

Greenstein et al., "Chem. of The Amino Acids", John Wiley & Sons, vol. 1, pp. 698–670 & vol III, pp. 2308–2375 (1961).
Sammes, Chem. Abst., vol. 72 #901102 (1970).
Davis, J. Org. Chem., vol. 43, pp. 3980–3982 (1979).
Sammes et al., J. Chem. Soc. C., 1971, pp. 2151–2155 (1971).

*Primary Examiner*—James H. Reamer

[57] ABSTRACT

A method for synthesizing alpha amino acids proceding through novel intermediates of the formulas:

$R_1R_2C(OSOCl)CN$, $R_1R_2C(Cl)CN$ and
$[R_1R_2C(CN)O]_2SO$ wherein $R_1$ and $R_2$ are each selected from hydrogen monovalent substituted and unsubstituted hydrocarbon radicals of 1 to 10 carbon atoms. The use of these intermediates allows the synthesis steps to be exothermic and results in an overall synthesis method which is faster than the snythesis methods of the prior art.

5 Claims, No Drawings

SYNTHESIS OF ALPHA-AMINO ACIDS

The invention was made in the course of or under U.S. Department of Energy Contract No. W-7405-ENG-48 with the University of California.

This is a division of application Ser. No. 77,811, filed Sept. 21, 1979, now abandoned.

BACKGROUND OF THE INVENTION

This invention relates to a new method for synthesizing alpha amino acids in which novel intermediates are utilized. More particularly, the principal distinguishing reaction is that of a cyanohydrin with thionyl chloride.

Alpha amino acids have been synthesized for a number of years. A major use of alpha amino acids is in vitamin supplements. Another use is in nuclear medicine wherein a synthesized alpha amino acid is labeled with a $^{11}C$ atom in the carboxyl group.

In U.S. Pat. No. 2,520,312 a method is disclosed for synthesizing amino acids. In particular, a cyanohydrin is converted to a corresponding amino nitrile by the action of ammonia at high temperature and pressure, an endothermic step. Of course, a synthesis of shorter duration and avoiding reacting under high pressure would be desirable.

It is another object of this invention to provide a new method for synthesizing alpha amino acids having both higher yields and lower pressure requirements than the prior art.

Another object of the invention is a synthesis which proceeds more rapidly than those of the prior art.

Yet another object is an alpha amino acid synthesis in which each step is exothermic so that the overall process is relatively fast.

SUMMARY OF THE INVENTION

In the present invention, a novel process for synthesizing alpha amino acids employs as a reactant, thionyl chloride (SOCl$_2$), and proceeds through novel intermediates. The process generally includes the steps of reacting an aldehyde or ketone with cyanide to generate a cyanohydrin, reacting the cyanohydrin with thionyl chloride at room temperature to generate a novel 2-chlorosulfinyl nitrile, reacting the novel 2-chlorosulfinyl nitrile with liquid ammonia to generate an alpha amino nitrile and hydrolyzing the alpha amino nitrile to produce an alpha amino acid.

The novel intermediates are of the formula:

R$_1$R$_2$C(OSOCl)CN, R$_1$R$_2$C(Cl)CN, and
[R$_1$R$_2$C(CN)O]$_2$SO, wherein R$_1$ and R$_2$ are each selected from hydrogen and monovalent substituted and unsubstituted hydrocarbon radicals of 1 to 12 carbon atoms as defined in more detail hereinafter and preferably methyl, ethyl, propyl, butyl or isobutyl. The last-mentioned sulfite intermediate above is a bis compound which can be symmetrical or asymmetrical.

DESCRIPTION OF THE PREFERRED EMBODIMENT

The general reaction scheme, scheme A, for the alpha amino acid synthesis of this invention is as follows:

  A

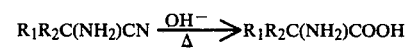

Among the monovalent substituted and unsubstituted hydrocarbon radicals, which R$_1$ and R$_2$ can be, are alkyl radicals (e.g., methyl, ethyl, propyl, butyl, isobutyl, decyl); aryl radicals (e.g., phenyl, naphthyl, biphenyl); alkaryl radical (e.g., tolyl, xylyl, ethylphenyl); aralkyl radicals (e.g., benzyl, phenylethyl), and alkenyl radicals (e.g., vinyl, methallyl), and p-hydroxybenzyl. The R$_1$R$_2$C(OSOCl)CN compounds are novel.

It is preferred that hydrocarbon radicals contains from 1-5 carbon atoms. It is further preferred that one of R$_1$ and R$_2$ be hydrogen.

Alternatively, but less preferred, the conditions of the thionyl chloride reaction can be modified so that the reaction proceeds through another intermediate which is also novel. This alternative reaction scheme, scheme B, is

  B

In addition, yet another alternative exists and follows the thionyl chloride step of scheme A. This alternative which may prove advantageous involves an additional intermediate step which yields a novel intermediate. This further step, scheme C, is

  C

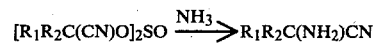

In more detail, the synthesis of the invention according to scheme A begins with reacting an aldehyde or ketone, both commonly available, with a metal cyanide, such as potassium or sodium cyanide, to yield a cyanohydrin. This reaction can be carried out at room temperature and pressure by suspending the metal cyanide in anhydrous ether, dissolving the aldehyde or ketone in glacial acetic acid, and then adding the dissolved aldehyde or ketone to the suspended metal cyanide dropwise. The reaction mixture is cooled with an ice bath. An almost quantitative conversion to the cyanohydrin occurs. The carrying out of this reaction in the absence of water is believed to be novel.

No special precautions are needed to exclude traces of water during the cyanohydrin generation. Water appears to be involved in the reaction, but only trace amounts appear necessary to drive it forward. Potassium cyanide typically contains some moisture leading to the reaction:

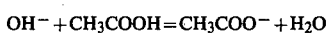

To separate the cyanohydrin product, filtration and distillation can be utilized. By-product acetate ion precipitates as metal acetate, i.e., potassium acetate. The presence of increased amounts of water, although not adversely affecting the yield, results in precipitated potassium acetate which is heavy and pasty and, hence, makes mixing difficult. A large volume of ether facilitates mixing and isolation of the product.

The precipitated potassium acetate can be removed by filtration from the solution. The filter cake should be washed several times with small portions of anhydrous ether which is added to the solution. The ether in the solution can be evaporated at room temperature and reduced pressure to leave the cyanohydrin product.

The next step in the synthesis yields a novel 2-chlorosulfinyl nitrile. Cyanohydrin is added slowly to a preferably stoichiometric equivalent amount of thionyl chloride over a period of time. The mixture is stirred and preferably kept at room temperature or below by means of a water bath. Higher temperatures favor the product of scheme B. If a stoichiometric excess of thionyl chloride is used, the mixture is preferably anhydrous. The reaction is rapid and smooth and a 90% of theory conversion of the cyanohydrin to the chlorosulfinyl nitrile product can be obtained. The product can be separated by means of fractional distillation. The product is removed as one of the overhead products.

Also formed by the reaction of thionyl chloride and a cyanohydrin are two other novel compounds. The residue of the distillation consists almost entirely of the sulfite corresponding to the chlorosulfinyl nitrile. This sulfite can also be prepared by treating the chlorosulfinyl nitrile with an excess of formamide, $HCONH_2$ (scheme C). The sulfite residue can be converted to the chlorosulfinyl nitrile by refluxing with $SOCl_2$ for 5 to 10 minutes or can be reacted with liquid ammonia at room temperature and normal pressure to bypass the chlorosulfinyl nitrile and yield the amino nitrile corresponding to the chlorosulfinyl nitrile, the next intermediate in the synthesis.

Another compound formed by the reaction of thionyl chloride with a cyanohydrin is the 2-chloronitrile (scheme C) corresponding to the chlorosulfinyl nitrile. This chloronitrile can be formed quantitatively by refluxing the reaction mixture of the cyanohydrin and thionyl chloride for 4 to 5 hours. After removal of excess $SOCl_2$, the product oil (chloronitrile) can be distilled at atmospheric pressure. This chloronitrile can be reacted with liquid ammonia at room temperature and normal pressure to yield the corresponding 2-amino nitrile, the next intermediate in the synthesis.

As indicated in preceding paragraphs, the next step is to convert the chlorosulfinyl nitrile to the corresponding amino nitrile. This reaction is highly exothermic and therefor the chlorosulfinyl nitrile is preferably added dropwise to anhydrous ammonia cooled with a dry ice-acetone bath. A vigorous reaction occurs. Upon completion, the excess ammonia is preferably removed by evaporation by allowing the mixture to warm to yield the amino nitrile.

This amino nitrile, in turn, is converted to the amino acid corresponding to this amino nitrile by refluxing the amino nitrile with sodium hydroxide. Alternatively, a mineral acid such as hydrochloric acid can be used for this hydrolysis, but base is preferred for most amino acids because there is no apparent tar formation and a chromatographically pure sample is obtained.

Below is a table of some common amino acids which can be synthesized with the process of this invention.

| TABLE OF ILLUSTRATIVE ALPHA AMINO ACIDS | | |
|---|---|---|
| Aldehyde or Ketone | Chlorosulfinyl nitrile | (Common Name) Amino Acid |
| $(CH_3)_2CHCHO$ | $(CH_3)_2CHCH(OSOCl)CN$ | (Valine) $(CH_3)_2CHCH(NH_2)COOH$ |
| $CH_3CHO$ | $CH_3CH(OSOCl)CN$ | (Alanine) $CH_3CH(NH_2)COOH$ |
| $C_6H_4OHCHO$ | $C_6H_4OHCH(OSOCl)CN$ | (Tyrosine) $C_6H_4OHCH(NH_2)COOH$ (Alanine -α Amino Butyric Acid) |
| $CH_3CH_2CHO$ | $CH_3CH_2CH(OSOCl)CN$ | $CH_3CH_2CH_2(NH_2)COOH$ (Norvaline) |
| $CH_3CH_2CH_2CHO$ | $CH_3CH_2CH_2CH(OSOCl)CN$ | $CH_3CH_2CH_2CH_2(NH_2)COOH$ |

EXPERIMENTAL PREPARATION OF VALINE

Isobutyraldehyde was purified by distillation just before use. A purified grade of thionyl chloride was further purified by distillation from about 10% of its weight of boiled linseed oil. The ammonia was dried by distillation from a small quantity of clean sodium. All other materials were reagent grade. All boiling points are uncorrected. The infrared spectra were determined on a Perkin Elmer 1R421 (liquid film between KBr plates).

2-Hydroxyisobutyronitrile

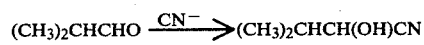

A well stirred suspension of 50 g of potassium cyanide in 800 ml of anhydrous ether was cooled in an icewater bath and 36.5 g of isobutyraldehyde in 45 ml of glacial acetic acid was added dropwise within 1 hour. A light voluminous precipitate of potassium acetate began to form immediately. After stirring for another hour the acetate was removed by filtration and the filter cake washed several times with small portions of anhydrous ether. The ether was removed from the combined filtrate and washings using a rotary evaporator at room temperature and reduced pressure. The remaining oil, 2-hydroxyisobutyronitrile, weighed approximately 50 g. It distilled without decomposition at 66°–67° C. and 0.1 mm pressure.

Anal. % Calcd. for $C_5H_9ON$: C, 60.60; H, 9.09; N, 14.14. Found: C, 60.62; H, 9.04; N, 14.12.

2-Chlorosulfinylisobutyronitrile

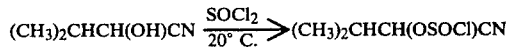

The cyanohydrin product (50 g) from the above preparation was added to 118 g of thionyl chloride over a period of 30 minutes while the mixture was stirred and kept at room temperature by means of a water bath. When the evolution of HCl had ceased, the excess thionyl chloride was removed under reduced pressure and the residue fractionated to yield an almost colorless oil, 2-chlorosulfinylisobutyronitrile, bp 40°–41° C. and 0.1 mm pressure as one of the cuts.

Anal. % Calcd. for $C_5H_8O_2NSCl$: C, 33.06; H, 4.40, S, 17.63; Cl, 19.53; N, 7.71. Found: C, 33.36; H, 4.48, S, 17.56; Cl, 19.51; N, 7.70.

The yield for a number of runs varied between 80 and 86 grams. The residue which remained was distilled and consisted almost entirely of the sulfite corresponding to the chlorosulfinyl nitrile, bp 97°–98° C. at 0.1 mm pressure.

Anal. % Calcd. for $C_{10}H_{16}O_3N_2S$: C, 49.18; H, 6.56; N, 11.47; S, 13.11. Found: C, 49.52; H, 6.63; N, 11.61; S, 12.86.

2-Chloroisobutyronitrile

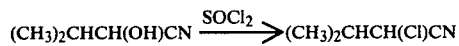
$(CH_3)_2CHCH(OH)CN \xrightarrow{SOCl_2} (CH_3)_2CHCH(Cl)CN$

Alternatively, the chlorosulfinyl nitrile (50 g) as prepared above was refluxed with 60 g of thionyl chloride for five hours after which the excess thionyl chloride was removed at atmospheric pressure. The residue was distilled at 149°–150° C. at atmospheric pressure to yield a colorless oil, 2 chloroisobutyronitrile, weighing 30 g.

Anal. % Calcd. for $C_5H_8NCl$: C, 51.08; H, 6.81; N, 11.91; Cl, 30.18. Found: C, 51.31; H, 6.85; N, 12.15; Cl, 29.86.

Isobutyronitrile sulfite

$(CH_3)_2CHCH(OSOCl)CN \xrightarrow{HCONH_2} [(CH_3)_2CHCH(CN)O]_2SO$ Also alternatively, the chlorosulfinyl nitrile (30 g) was added to 30 ml of formamide and the mixture shaken for several minutes until the resulting exothermic reaction was complete. The mixture was poured into water (100 ml) and the oil extracted with either. The ether solution was washed twice with two 20 ml portions of water and dried over anhydrous sodium sulfate. Upon removal of ether and distillation of the residue there was obtained 18 g of a colorless oil, isobutyronitrile sulfite, bp 97°–98° C. at 0.1 mm.

Anal. % Calcd. for $C_{10}H_{16}O_3N_2S$: C, 49.18; H, 6.56; N, 11.47; S, 13.11. Found: C, 49.09, H, 6.62; N, 11.59; S, 13.15.

Valine

$(CH_3)_2CHCH(OSOCl)CN \xrightarrow{NH_3}$ $(CH_3)_2CHCH(NH_2)CN \xrightarrow{OH^-} (CH_3)_2CHCH(NH_2)COOH$
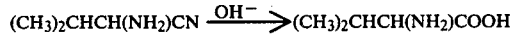

To approximately 35 ml of anhydrous ammonia cooled with a dry ice-acetone bath was added dropwise 18 g of the 2-chlorosulfinylisobutyronitrile. A vigorous reaction occurs and when complete, the cooling bath was removed and the ammonia allowed to evaporate. To the resulting residue was added 75 ml of absolute ethyl alcohol and the mixture heated to reflux. On cooling, 20 g of NaOH in 100 ml of water was added and the temperature increased to above 90° C. allowing the alcohol to distill off. The mixture was refluxed for 24 hr. After cooling, 100 ml of 6N HCl was added and the mixture taken to dryness under reduced pressure. A few ml of water was added to the residue and it was again taken to dryness. The residue was extracted several times with a total of 200 ml of hot absolute ethyl alcohol. The alcoholic solution was concentrated to approximately 50 ml, filtered and treated with 15 ml of pyridine. After standing in the refrigerator overnight the crystals were collected, washed with alcohol and air dried. The yield for several runs was from 8 to 9 g of very pure almost colorless valine. Paper chromatography showed the sample to be homogeneous having the same Rf value as a standard sample of valine (n-butanol; acetic acid; water; pyridine; 10, 2, 2, 1).

Anal. % Calcd. for $C_5H_{11}O_2N$: C, 51.28; H, 9.4; N, 11.96. Found C, 50.90; H, 8.96; N, 11.99.

I claim:

1. An improved process for synthesizing an alpha-amino acid comprising:

reacting a metal cyanide with an aldehyde or a ketone in the absence of water to form a corresponding cyanohydrin of the formula:

$R_1R_2C(OH)CN$
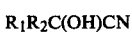

wherein $R_1$ and $R_2$ represent hydrogen, alkyl radicals of 1 to 10 carbon atoms, alkenyl radicals of 2 to 4 carbon atoms, aryl radicals of 6 to 12 carbon atoms, alkaryl radicals of 7–8 carbon atoms, aralkyl radicals of 7–8 carbon atoms, and p-hydroxyphenyl radicals, reacting said cyanohydrin with thionyl chloride to form a chlorosulfinyl nitrile of the formula:

$R_1R_2C(OSOCl)CN$,

reacting said chlorosulfinyl nitrile with formamide to form a nitrile sulfite of the formula:

$[R_1R_2C(CN)O]_2 SO$,

reacting the nitrile sulfite so formed with ammonia to form an amino nitrile of the formula:

$R_1R_2C(NH_2)CN$; and

hydrolyzing said amino nitrile to the alpha-amino acid.

2. A process according to claim 1 wherein $R_1$ is hydrogen and $R_2$ is an alkyl radical of 1 to 10 carbon atoms.

3. A process according to claim 1 wherein $R_1$ and $R_2$ are each as alkyl radical of 1–10 carbon atoms.

4. A process of claim 1 wherein $R_1$ and $R_2$ are each selected from hydrogen, methyl, ethyl, propyl, butyl, isobutyl, benzyl, and p-hydroxyphenyl.

5. A process according to claim 4 or 1 wherein one of $R_1$ and $R_2$ is hydrogen.

* * * * *